(12) United States Patent
Ugai et al.

(10) Patent No.: US 7,473,342 B2
(45) Date of Patent: Jan. 6, 2009

(54) CAPILLARY ARRAY AND CAPILLARY ELECTROPHORESIS APPARATUS

(75) Inventors: Seiichi Ugai, Hitachinaka (JP); Tomonari Morioka, Hitachinaka (JP); Ryoji Inaba, Hitachinaka (JP); Akihiro Suzuki, Hitachinaka (JP); Yoshinori Ookoshi, Hitachiomiya (JP); Yoshiyuki Okishima, Minori (JP); Tsukasa Ohira, Hitachinaka (JP); Motohiro Yamazaki, Mito (JP); Takashi Gomi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 109 days.

(21) Appl. No.: 11/395,158

(22) Filed: Apr. 3, 2006

(65) Prior Publication Data
US 2006/0219559 A1    Oct. 5, 2006

(30) Foreign Application Priority Data
Apr. 5, 2005    (JP)    ............................ 2005-108340

(51) Int. Cl.
*G01N 27/00*    (2006.01)
(52) U.S. Cl. ...................................... 204/601; 204/605
(58) Field of Classification Search .................. 204/601
See application file for complete search history.

(56) References Cited
U.S. PATENT DOCUMENTS

| | | | |
|---|---|---|---|
| 6,319,705 B1 * | 11/2001 | Tanaka | 435/287.1 |
| 6,562,214 B1 * | 5/2003 | Amrhein et al. | 204/601 |
| 6,856,390 B2 * | 2/2005 | Nordman et al. | 356/344 |
| 6,936,152 B2 * | 8/2005 | Kojima et al. | 204/601 |
| 7,250,099 B2 * | 7/2007 | Mooney et al. | 204/603 |
| 2002/0003091 A1 * | 1/2002 | Kojima et al. | 204/603 |
| 2002/0023839 A1 * | 2/2002 | Inaba et al. | 204/451 |
| 2003/0098239 A1 * | 5/2003 | Anazawa et al. | 204/603 |
| 2004/0112749 A1 * | 6/2004 | Shibasaki et al. | 204/601 |
| 2004/0200723 A1 * | 10/2004 | Sakai et al. | 204/451 |

* cited by examiner

*Primary Examiner*—Nam X Nguyen
*Assistant Examiner*—Dustin Q Dam
(74) *Attorney, Agent, or Firm*—McDermott Will & Emery LLP

(57) ABSTRACT

In a case where the temperature of capillaries cannot be controlled rapidly in accordance with the change of the amount of heat generated from the capillaries, the phoretic speed of the sample is not controlled constant to lower the analyzing performance for the sample. This invention intends to stabilize the electrophoretic speed. The surface of a substrate on which a plurality of capillaries are arranged is in contact with a member capable of temperature control thereby controlling the temperature of the capillaries. Since a member capable of controlling the temperature and the capillaries are in direct contact with each other according to the invention, the temperature of the capillary can be controlled rapidly at a high accuracy, so that electrophoretic speed is stabilized.

11 Claims, 13 Drawing Sheets

Spectralizing treatment

US 7,473,342 B2

CAPILLARY ARRAY AND CAPILLARY ELECTROPHORESIS APPARATUS

CLAIM OF PRIORITY

This application claims priority under 35 U.S.C. §119 from Japanese Patent Application No. 2005-108340, filed on Apr. 5, 2005, the entire contents of which are hereby incorporated by reference herein.

FIELD OF THE INVENTION

The present invention relates to a technique of separating and analyzing nucleic acids, proteins, etc. by electrophoresis and to, for example, a capillary array electrophoresis apparatus.

BACKGROUND OF THE INVENTION

A capillary array electrophoresis apparatus includes, basically, a capillary array having a plurality of capillaries, a power supply for applying a high voltage on both ends of the capillary, an excitation optical system comprising a laser light source or the like, and a photo-receiving optical system for detecting fluorescence. Upon analysis of a sample, a sample such as a fluorescence-labeled DNA is electrophoresed and separated in the order of molecule size, and an irradiation light is applied to the labeled sample to detect emitted fluorescence. The capillary array electrophoresis apparatus provides a high separation speed for samples, can analyze plural samples simultaneously and can meet the demand of analysis such as for DNA and proteins which has been required more and more in recent years.

U.S. Pat. No. 6,562,214 discloses an electrophoresis apparatus in which a capillary array formed by laminating plural capillaries to two sheets are in contact with a heater.

SUMMARY OF THE INVENTION

In U.S. Pat. No. 6,562,214, the capillary and the heater are in contact with each other by way of the sheet. Heat generated by the heater once diffuses into the sheet and then conducts to the capillary. Accordingly, temperature of the capillary cannot be controlled rapidly.

In the capillary electrophoresis, electrophoretic analysis is started after heating the capillary to a predetermined temperature but, in a case where it takes a long time till the capillary reaches a predetermined temperature, the throughput of the analysis is worsened.

Further, upon electrophoretic separation of a sample by the capillary, the capillary itself is applied with a voltage and also generates heat. In a case where the temperature of the capillary cannot be controlled rapidly in accordance with the change of the amount of heat generated from the capillary, the phoretic speed of the sample is not controlled at a constant rate so that the performance for the analysis of the sample must be lowered.

The present invention intends to rapidly stabilize the capillary temperature.

In accordance with the invention, the surface of a substrate on which plural capillaries are arranged is in contact with a member that can be controlled for the temperature thereby controlling the temperature of the capillary.

According to the invention, since the capillary is in direct contact with the member capable of temperature control, the temperature of the capillary can be controlled rapidly and accurately to stabilize the electrophoretic speed.

DETAILED DESCRIPTION OF THE PREFERRED EMBODIMENTS

The foregoing and other novel features and advantages of the present invention are to be described with reference to the drawings. The drawings are for exclusively illustration and not defining the scope of the invention, and each of examples can be combined properly.

First Embodiment

Figure 1:
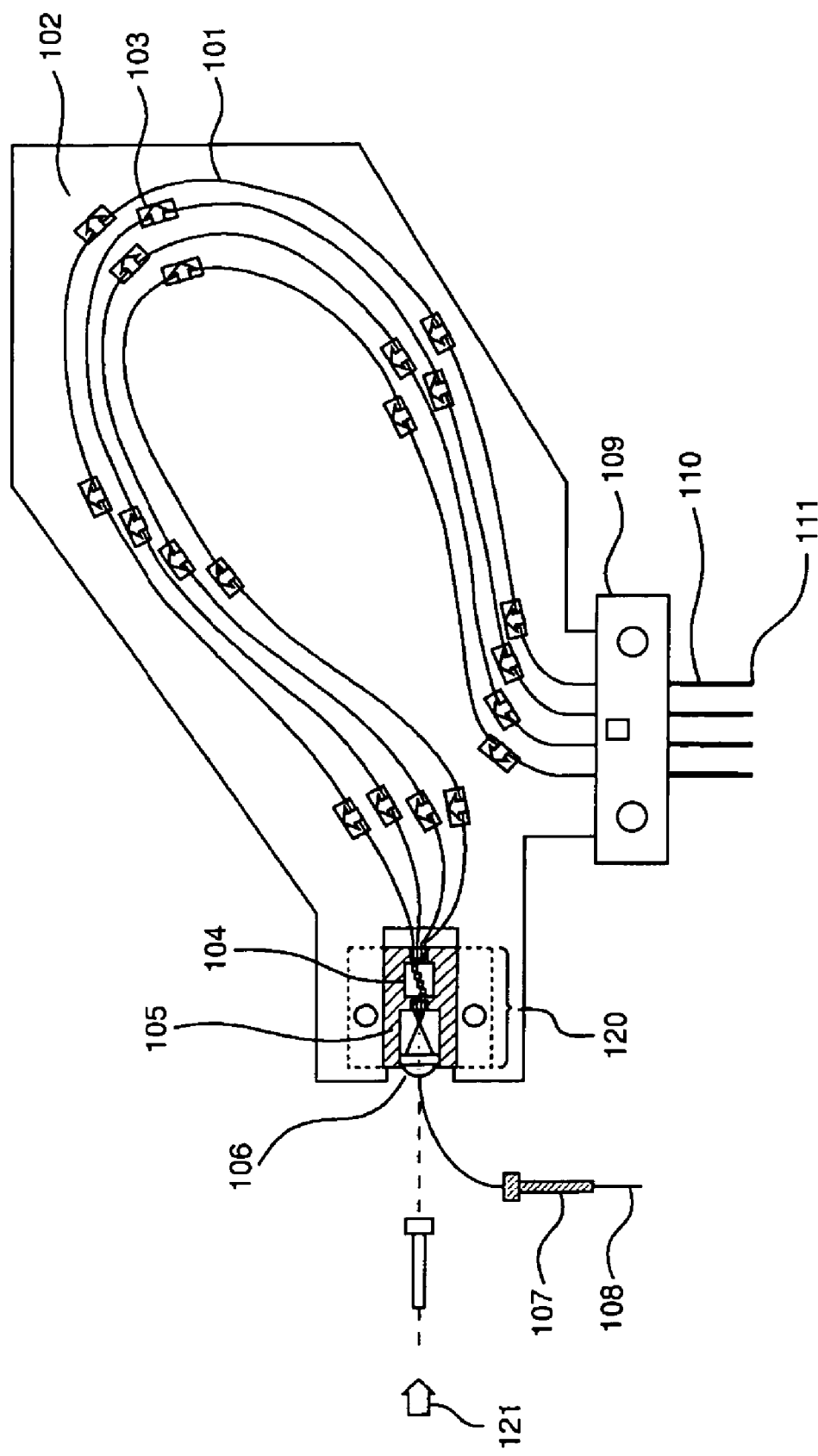
FIG. 1 is a schematic view of a capillary array of Example 1.

FIG. 1 shows a schematic view of a capillary array in this embodiment. The capillary array includes a support plate 102, capillaries 101 by the number of about 1 to 16, electrodes 110, an electrode holder 109, a capillary head 107, and a fluorescence detection section 120. The capillaries 101 are fixed to the support plate 102 and the electrode holder 109 and the detection 120 are also attached to the support plate 102.

The capillary 101 has a hollow glass tube and a polyimide coating in which phoretic medium such as a gel can be filled to form a phoretic channel for electrophoretically separating a sample. The capillaries 101 by the number of about 1 to 16 are retained by clips 103 to the support plate 102 which is a plastic plate of about several hundreds μm to several mm thickness and are substantially kept the extended loop shape. This can stabilize the position for the capillaries upon attachment to an apparatus main body and avoid disadvantage that the capillaries overlap with each other or are flexed being caught by the door of the main body oven. Further, since the capillaries are fixed to a sheet of the support plate 102, one surface of which can be in direct contact with a heater of the oven to enhance the heat conductivity, the electrophoretic speed can be stabilized.

Electrodes 110 are provided corresponding to a plurality of capillaries 101 and held by an electrode holder 109 as an electrode holding member. The sample can be introduced into the capillaries 101 and the sample can be electrophoretically separated by generation of electric fields. The electrode 110 is, for example, made of a stainless pipe with an inner diameter of about 0.1 to 0.5 mm, into which the capillary is inserted. The capillary 101 is fixed to the electrode 110 at the electrode top end 111 and sealed with an adhesive.

The detection section 120 includes a condensing lens 106 for condensing excitation light 121 such as from LED or laser and introducing the same to the capillary, a substrate 104 apertured with windows for detecting fluorescence and a detection base plate 105 for fixing the members, and fixed loosely to the support plate with a clearance to some extent. This is because the fluorescence detection section (camera, CCD, etc.) on the side of the apparatus and the detection window 104 have to be positionally aligned, which requires a margin to some extent. While holes are formed in the detection base plate 105 and the support plate 102 into which fixing pins are inserted to hold both of them, and the holes for either the detection base plate or the support plate are apertured somewhat larger so as to provide a clearance. Further, a recess may be formed to a portion of the support plate near the detection section so as to facilitate the movement of the detection section. Alternatively, a method of positionally aligning the detection window 104 accurately by withdrawing fixing pins upon setting to the apparatus may also be adopted.

Further, the capillary head 107 for injection of a polymer as a phoretic medium bundles and holds injection ends of phoretic medium of plural capillaries 101 and can be attached to or detached from a phoretic medium filling mechanism of the electrophoretic apparatus. Further, at the injection end of the phoretic medium a capillary protrusion 108 protruded from the capillary head 107 is directed downward. With the constitution described above, upon injection of the polymer, bubbles remaining between the phoretic medium filling mechanism and the capillary head cannot be present near the capillary protrusion and the bubbles are less involved.

Figure 2:
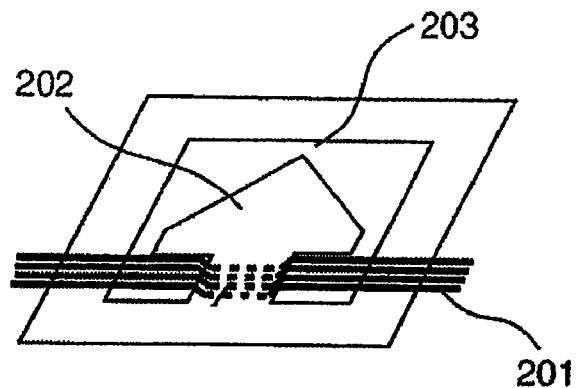
FIGS. 2A, 2B, and 2C show examples of a clip formed to a support plate.
Figure 2:
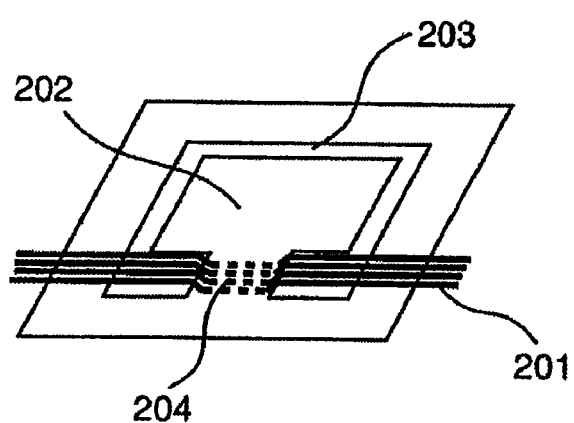
Figure 2:
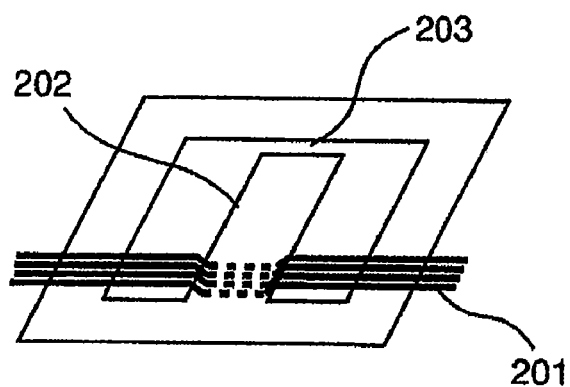

FIG. 2A to FIG. 2C show examples of clips 103 formed on the support plate 102. Capillaries 201 are passed from an introduction port 203 and fixed (supported) by a capillary retainer 202. As a result of an experiment, while they may be retained simply by a rectangular shape as shown in FIG. 2C, they somewhat tend to be detached easily. Such detachment can be prevented by widening the capillary retainer 202 on the side of the capillary as shown in FIG. 2B. Further, the structure easy for insertion and less detaching can be obtained by pointing the top end as shown in FIG. 2A. The structure for the support plate and the clip can be manufactured by punching a plastic substrate, for example, made of polyethylene, polystyrene, and polybutylene terephthalate of a thickness from several hundred micrometers to several millimeters. While the capillaries 101 are fixed by all of the clips 103 formed on the support plate 102, the capillaries may not always be fixed by all of the clips in a case where the length of the capillary 101 is short.

Figure 14:
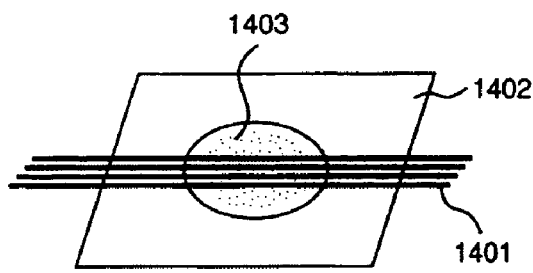
FIGS. 14A, 14B, 14C, and 14D are views for explaining a method of partial fixing to a support plate.
Figure 14:
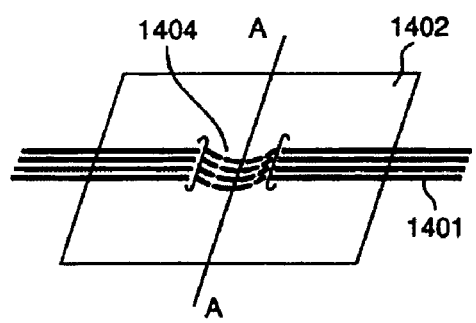
Figure 14:
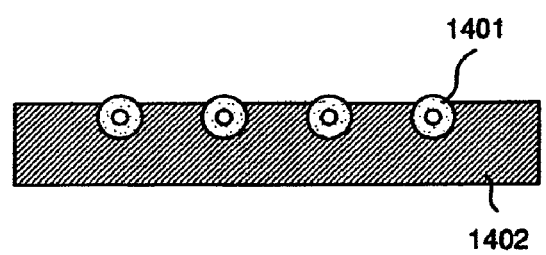
Figure 14:
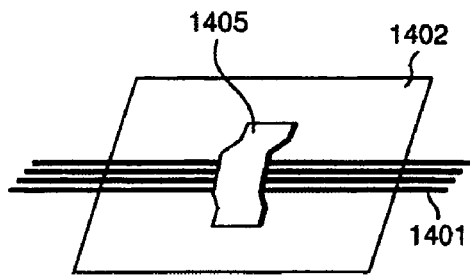

Further, the capillary is fixed to the support plate not by the clip means but partially by means of an adhesive 1403 as shown in FIG. 14A. This can provide heat dissipation about to the same extent as obtained by the clip means. For example, the capillary array can be formed easily by using a UV cure type resin. Alternatively, as shown in FIG. 14B and FIG. 14C (A-A cross section in FIG. 14B), the capillaries 1401 may be partially buried by hot press bonding them in the plastic substrate at capillary bury portions 1404. This can firmly fix the capillary 1401 to the support substrate 1402 and, further, since the capillary fixing portions have flatness, this can improve contact with the surface heater of the electrophoretic apparatus to control the temperature at higher accuracy. Further, the capillary may also be press bonded by a small heat piece 1405 different from the support substrate as shown in FIG. 14D. This can facilitate the preparation of the capillary array and relatively flatter at the capillary fixing portions.

Figure 3:
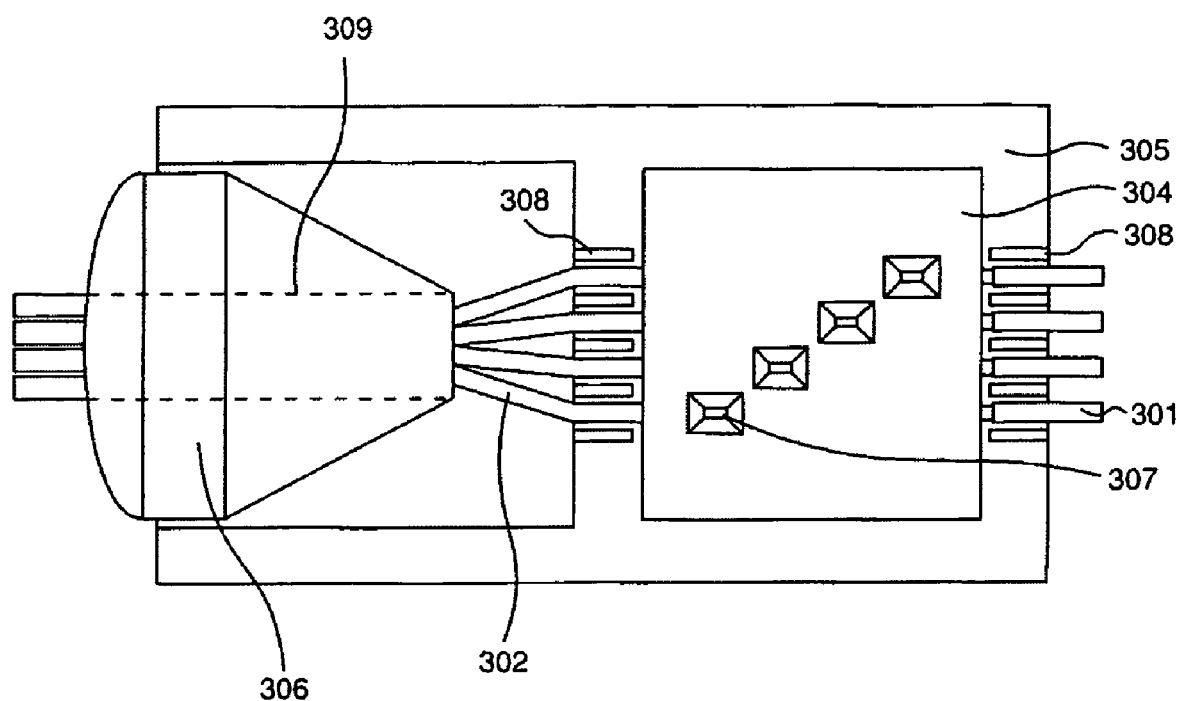
FIG. 3 is an explanatory view of a window plate.

Then, the detection section is to be described specifically with reference to FIG. 3. The detection section includes a condensing lens 306 made of glass or polymethyl methacrylate for condensing an excitation light, in which a through hole 309 is provided at the center thereof. The capillaries 301 are assembled by being passed through the through hole 309. The capillaries 301 arranged side by side are covered with a window plate 304 as a light screening member provided with window holes 307 for transmitting fluorescence from a sample and prevents cross-talk of fluorescence. The window hole 307 may also be constituted not as a physical aperture but by forming only the desired regions with a light transparent member. In the regions for the condensing lens 306 and the window plate 304 for taking out fluorescence, coating for the capillaries is removed to expose quartz tubes 302 for suppressing the decay of the excitation light. A capillary guide 308 is formed on a detection base plate 305 such that the capillaries are arranged in the fluorescence detection region. Further, window holes 307 are apertured stepwise in the window substrate 304.

Figure 4:
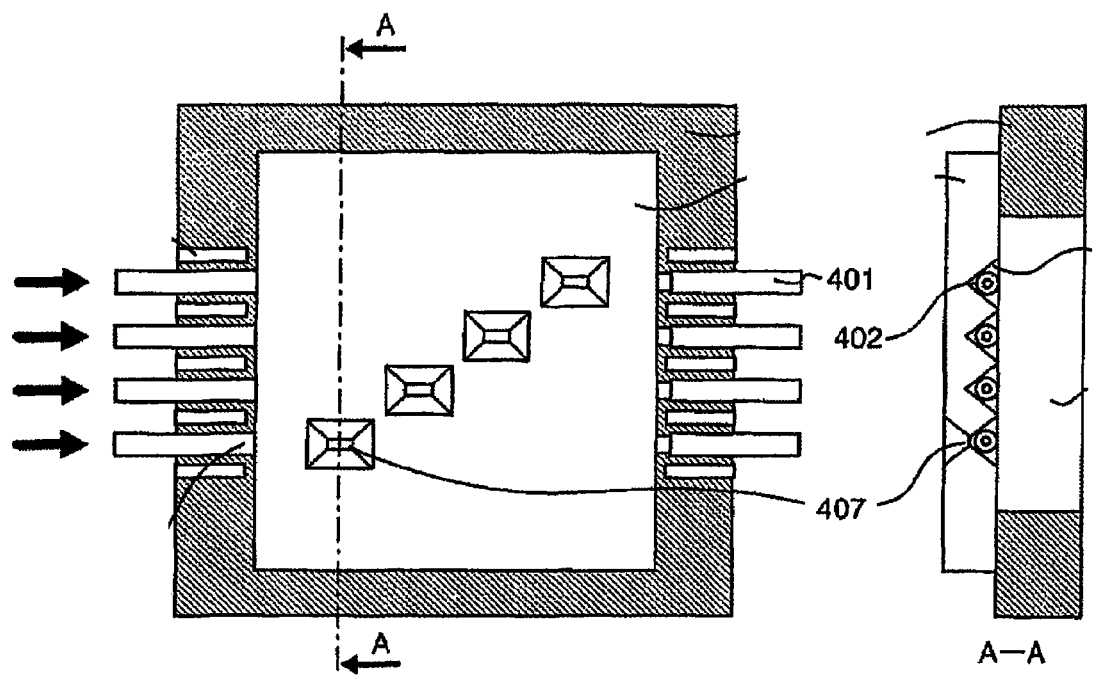
FIG. 4 is a view explaining the arrangement of window holes in the window plate.
Figure 4:
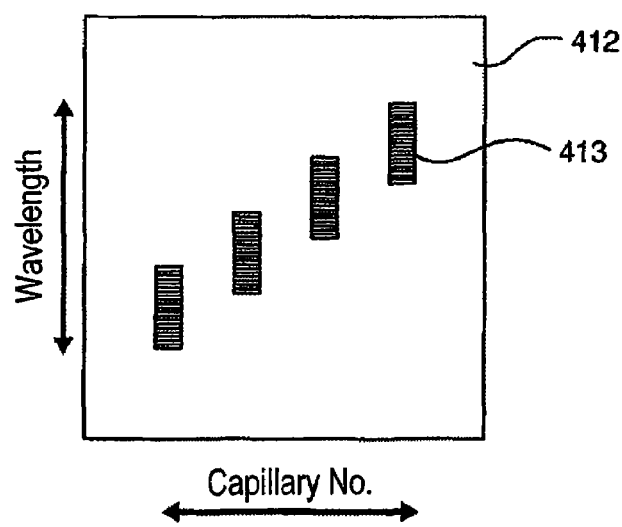

FIG. 4 is a view for explaining the arrangement of the window holes in the window plate and description to be made for the advantage of arranging the window holes stepwise. It is necessary that the fluorescence emitted from the sample in the capillary has to be spectralized in the direction substantially perpendicular to the central axis of the capillary by using, for example, a grating. However, in a case where the window holes 407 are formed along one straight line, spectral images 413 projected on a CCD 412 overlap to each other. In order to avoid the overlap, the window holes are formed stepwise. Arrangement for the window holes is not always restricted to the stepwise arrangement but may also be in other arrangement providing that the plurality of detection windows are not arranged in the direction substantially perpendicular to the capillary 401.

Figure 5:
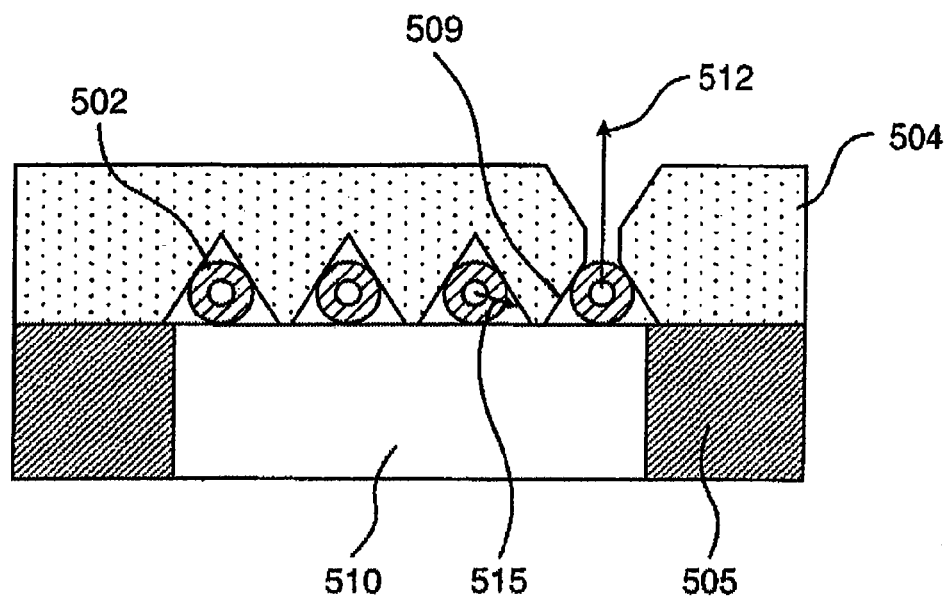
FIG. 5A and FIG. 5B are views explaining the effect of a V-groove in the window plate.
Figure 5:
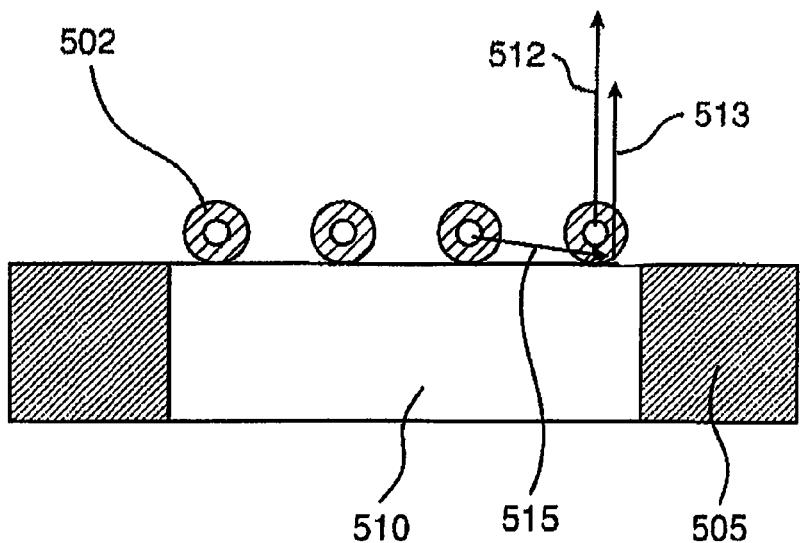

FIG. 5A shows a cross sectional shape of the window plate and the effect thereof. The window plate 504 is formed by applying, for example, anisotropic etching to single crystal silicon. A capillary quartz tube 502 is positioned by a V-groove 509 fabricated in the window plate 504 and the V-groove is recessed deeply such that the capillary is substantially covered. Use of the window plate as described above provides an effect that a single light 512 passes straightly through the window but the fluorescence 515 from adjacent capillaries can be cut by the V-shaped slope 509. Further, by forming an opening 510 to the detection plate 505, reflection light from the lower surface can also be eliminated to greatly decrease cross-talk. On the other hand, as shown in FIG. 5B, in a case of not using the window plate 504, the fluorescence 515 from the adjacent capillary undergoes scattering from the glass surface to generates a cross-talk light 513. Further, in a case of using a single capillary, since the problem of cross-talk due to the adjacent capillary is not made, it is not always necessary to use the window plate 504.

Figure 6:
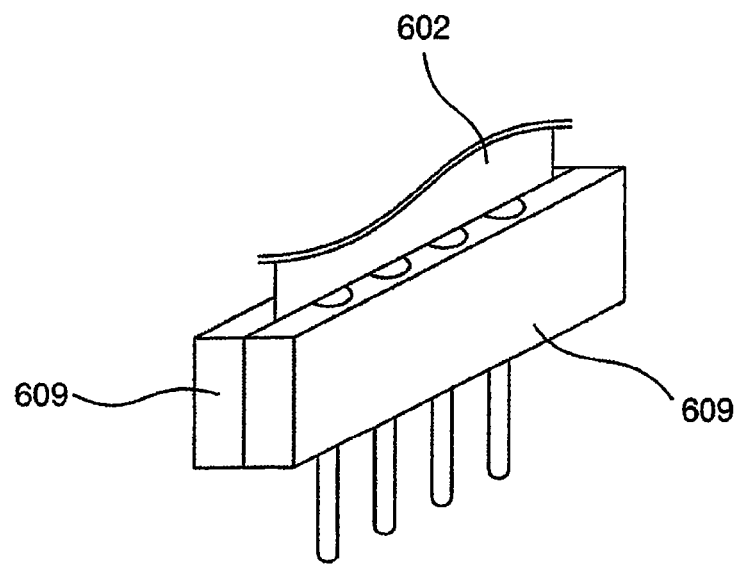
FIG. 6 is a view explaining an electrode integrated with a window plate.
Figure 7:
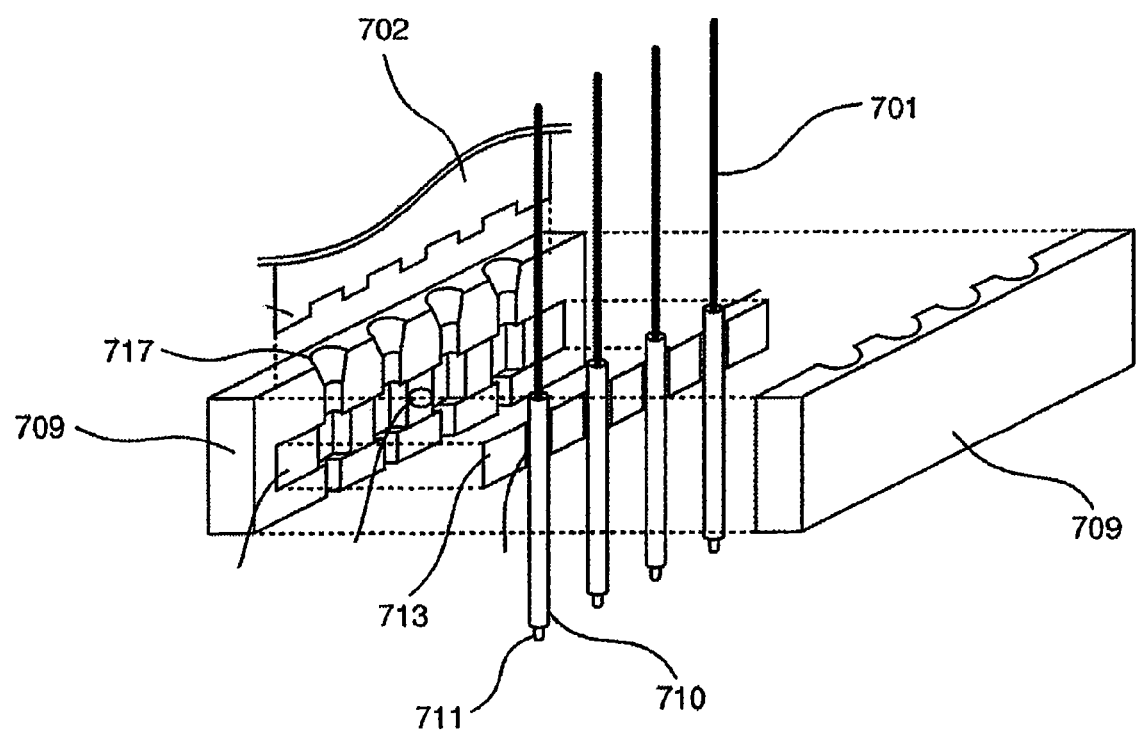
FIG. 7 is an exploded view of an electrode integrated with a support plate.

FIG. 6 shows a structure in which a support plate 602 and an electrode holder 609 are assembled integrally. A support plate 602 is assembled being sandwiched between two sheets of an electrode holder 609. FIG. 7 is an exploded view of the structure given by FIG. 6 (also with capillaries). Electrodes made of stainless steel, etc. are previously conducted electrically and fixed to a common electrode 713 by caulking, etc. The electrode and the support substrate 702 are sandwiched by the electrode holder and fixed and integrated by means of adhesion or ultrasonic welding. In this case, a process of inserting the capillary 701 subsequently to a member formed by integrating the electrode and the support plate and bonding to secure the electrode top end 711 is adopted. Flares 717 formed on an electrode holder 709 and flares formed to an electrode 710 are used for facilitating insertion of the capillary 701 in the electrode 710. The support plate put between the electrode holders can provide an advantage capable of firmly fixing both of them.

Figure 8:
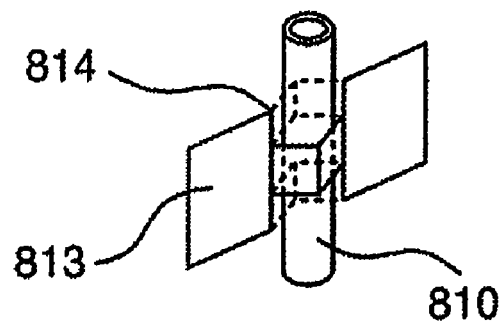
FIGS. 8A, 8B, and 8C are views explaining a method of fixing an electrode and a common electrode.
Figure 8:
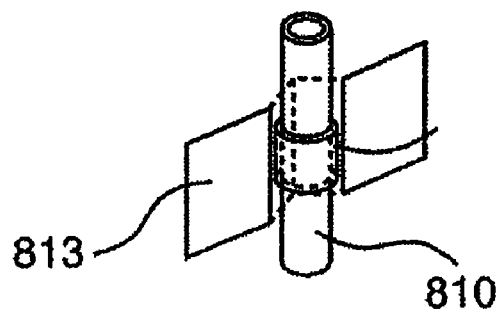
Figure 8:
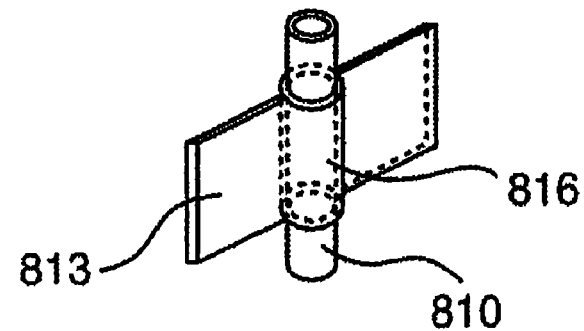

FIGS. 8A to 8C show an example of the method of fixing an electrode 810 and a common electrode 813. The electrode 810 can be electrically connected by way of a common electrode 813 to a power supply of an electrophoretic apparatus. FIG. 8A shows a method of assembling by enforcing the electrode 810 in the common electrodes 813 in which an upward V-shape and a downward V-shape are formed and establishing electric conduction by the pressure of contact of an electrode enforcing portion 814. FIG. 8B shows a method of electrically conducting a common electrode 813 formed with a V-shape and an electrode 810 by means of a conductive adhesive. FIG. 8C shows a method of using a conductive plastic 816 for electrical conduction portion between the common electrode 813 and the electrode 810. It may also be integrally molded by selecting the same material as that of the conductive plastic 816 as the material for forming the common electrode 813.

Figure 13:
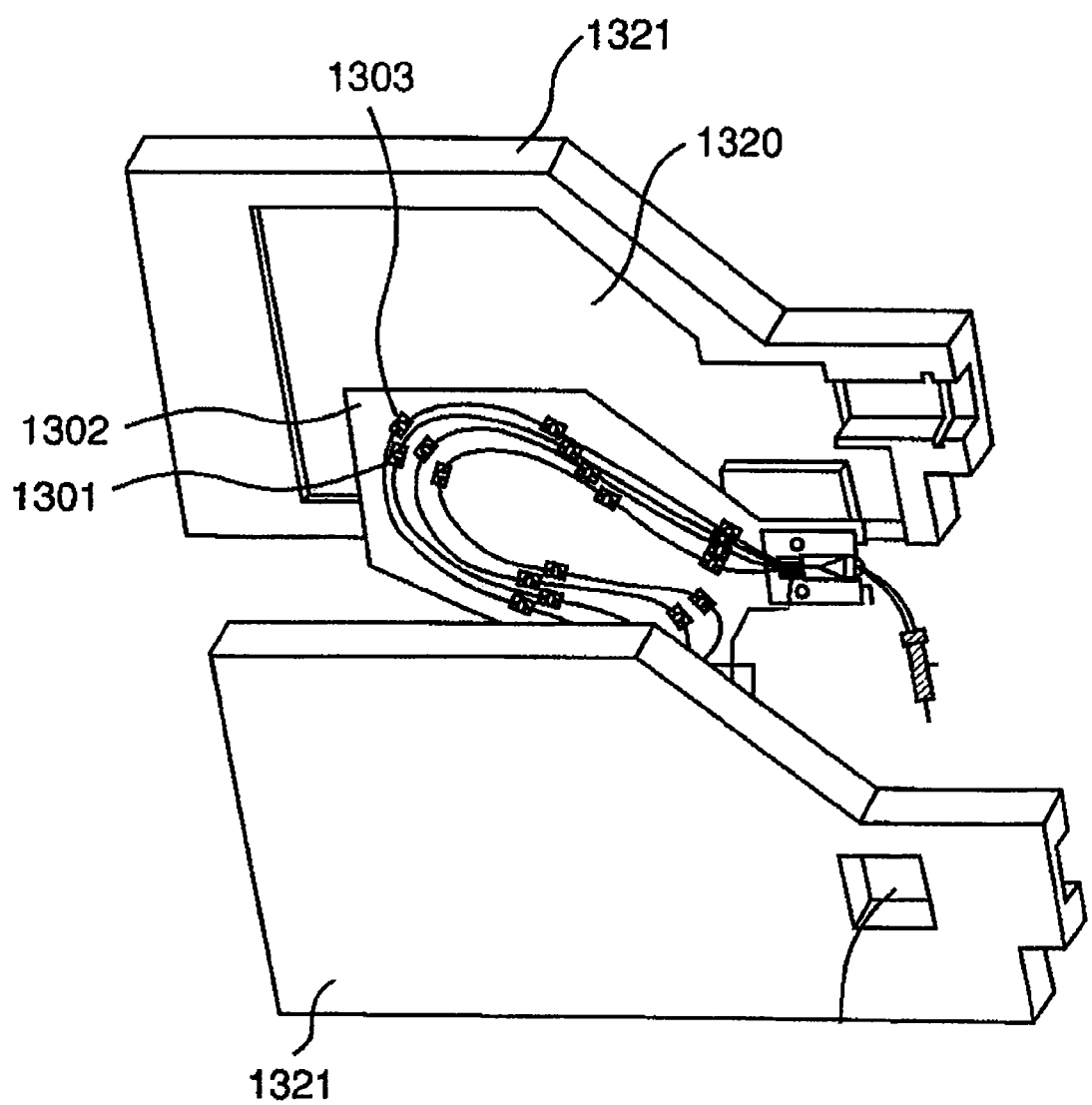
FIG. 13 is a view for explaining attachment to an oven.

Then, attachment of the capillary array to the main body of the apparatus will be described with reference to FIG. 13. A surface heater 1320 is disposed to an oven casing 1321, which has a power of elevating the temperature usually to 50 to 60° C. for increasing and stabilizing the phoretic speed. The oven has a structure of putting the capillary support plate 1302 by the heater 1320 and the lid of the oven, to contact the capillary 1301 and the heater with each other. Such an attachment structure provides a merit capable of giving good heat response and temperature distribution and decreasing the volume compared with an air conditioning system.

In this embodiment, since the capillaries are laid around on one surface of the plate, the capillaries can be in direct contact with the heater. Accordingly, the temperature of the capillary can be controlled rapidly and reliably. Further, this can prevent disadvantage that the capillary is caught by the apparatus main body and flexed upon handing the capillary array.

Further, in this embodiment, the capillaries are arranged on the support plate such that they do not intersect with each other. In a case where capillaries intersect with each other, an excess force exerts on the intersections of the capillaries upon sandwiching the support plate by the heater and the lid to possibly flex the capillaries. However, according to this embodiment, the capillary array can be mounted easily and reliably to the electrophoresis apparatus.

Further, in this embodiment, since the capillaries are fixed being pinched by the clip or the like so that they are fixed to the plate, this facilitates manufacture and improves the productivity of the capillary array.

Further, in this embodiment, the detection base plate for arranging and disposing the excitation light irradiation portion of the capillaries and the support plate for supporting the capillaries are formed as separate members. This enables to separately prepare the detection base plate requiring high optical accuracy and the detection base plate only requiring to fix the capillaries and the productivity of the capillary array can be increased.

Further, in this embodiment, the detection base plate and the electrode holder are integrated with the support plate. If the three parts were separated individually and merely connected by the capillaries, this would result in handling inconvenience to a user upon attaching the capillary array to the electrophoretic apparatus. That is, it would be necessary for the user to attach the detection base plate by one hand while supporting two other parts, i.e., the support plate and the electrode holder by the other hand. Further, depending on the way of user's handling, it may sometimes result in disadvantage of exerting an excess load on the capillaries to flexural damages. However, in a case where they are integrated as in this embodiment, handling property upon attaching the capillary array can be improved greatly.

Further, in this embodiment, the electrode holder has a structure of joining two sheets of members, and a support plate is put and fixed between the two sheets of members. This can firmly fix the electrode holder and the support plate.

Further, in this embodiment, the capillary top end protrudes longer than the capillary head and plural phoretic medium injection ends are directed downward when the capillary head is connected to the phoretic medium filling mechanism, thereby providing an effect capable of decreasing the involvement of bubbles during electrophoresis. If bubbles enter the inside of the capillary, a high voltage is applied across both ends of a bubble to result in sparking which may possibly hinder electrophoresis. However, in this embodiment, even when bubbles intruding in the phoretic medium filling mechanism approach the capillary top end while ascending, they pass the capillary top end, further ascend and remain. Thus, bubbles do not intrude in the capillary.

Second Embodiment

The second embodiment of the invention is an example of manufacturing an electrode with a single part and attaching the same subsequently. Description is to be made mainly for the difference from the first embodiment.

Figure 9:
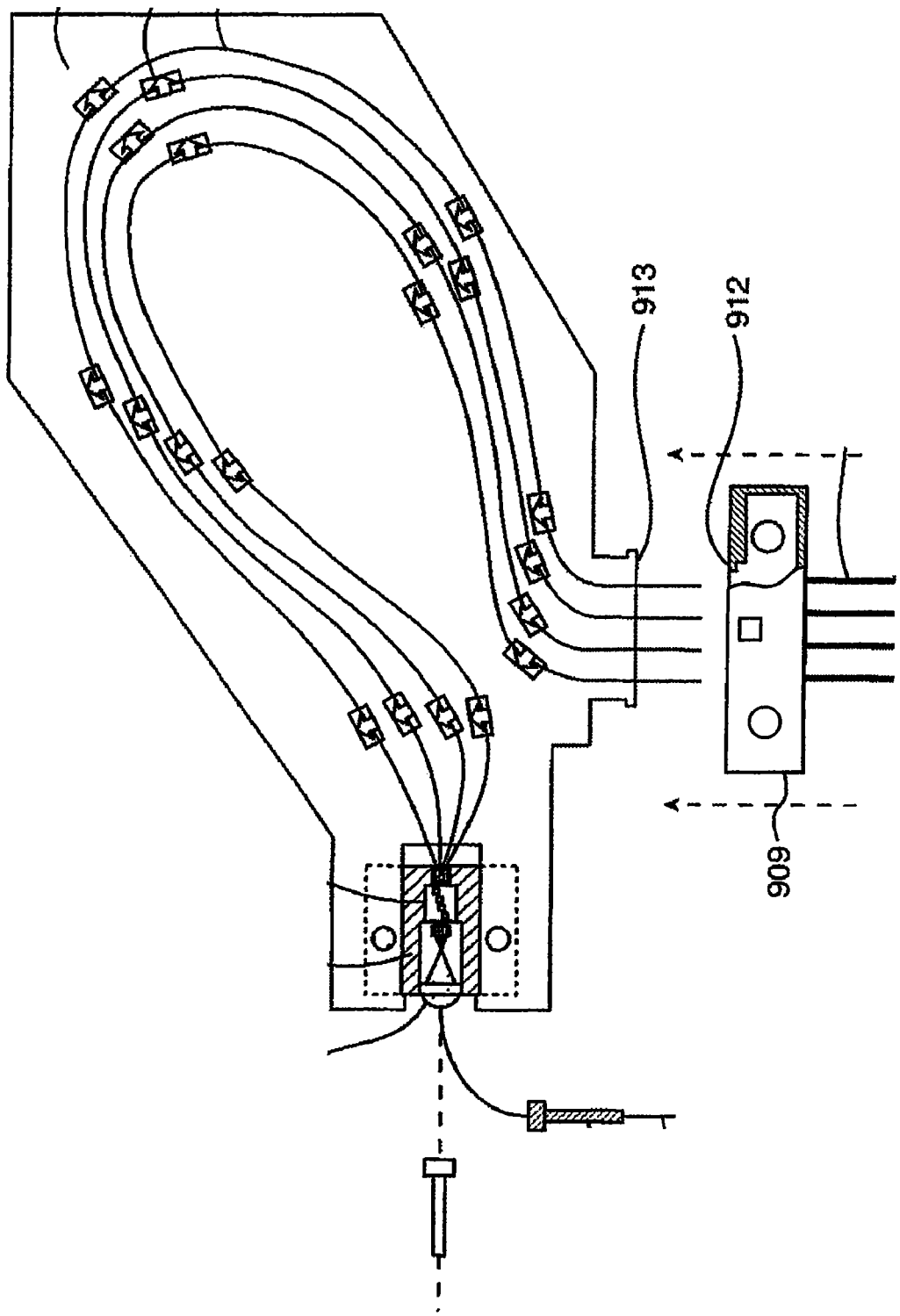
FIG. 9 shows an example of disposing a hook to an electrode holder.

In FIG. 9, a concave hook 912 is formed inside an electrode holder 909 and a convex hook 913 is also formed on the side of the electrode of a support base. When the electrode holder is inserted in the direction of an arrow in the drawing, the support plate and the electrode holder can be fixed simply. Both of them may be further bonded and fixed more firmly.

This embodiment has a structure capable of inserting the support plate into the electrode holder and a hook structure is formed on a portion of the electrode holder insertion port and on a portion of the support plate so that they are fixed. With the hook structure formed on the portion of the support plate, both of them can be integrated by merely inserting the support plate into the electrode holder to facilitate assembling of the capillary array.

Third Preferred Embodiment

A third embodiment of the invention is an example of securing an electrode holder and a support plate by fixing pins and attaching an electrode subsequently. Description is to be made mainly for the difference between the first embodiment and the second embodiment.

Figure 10:
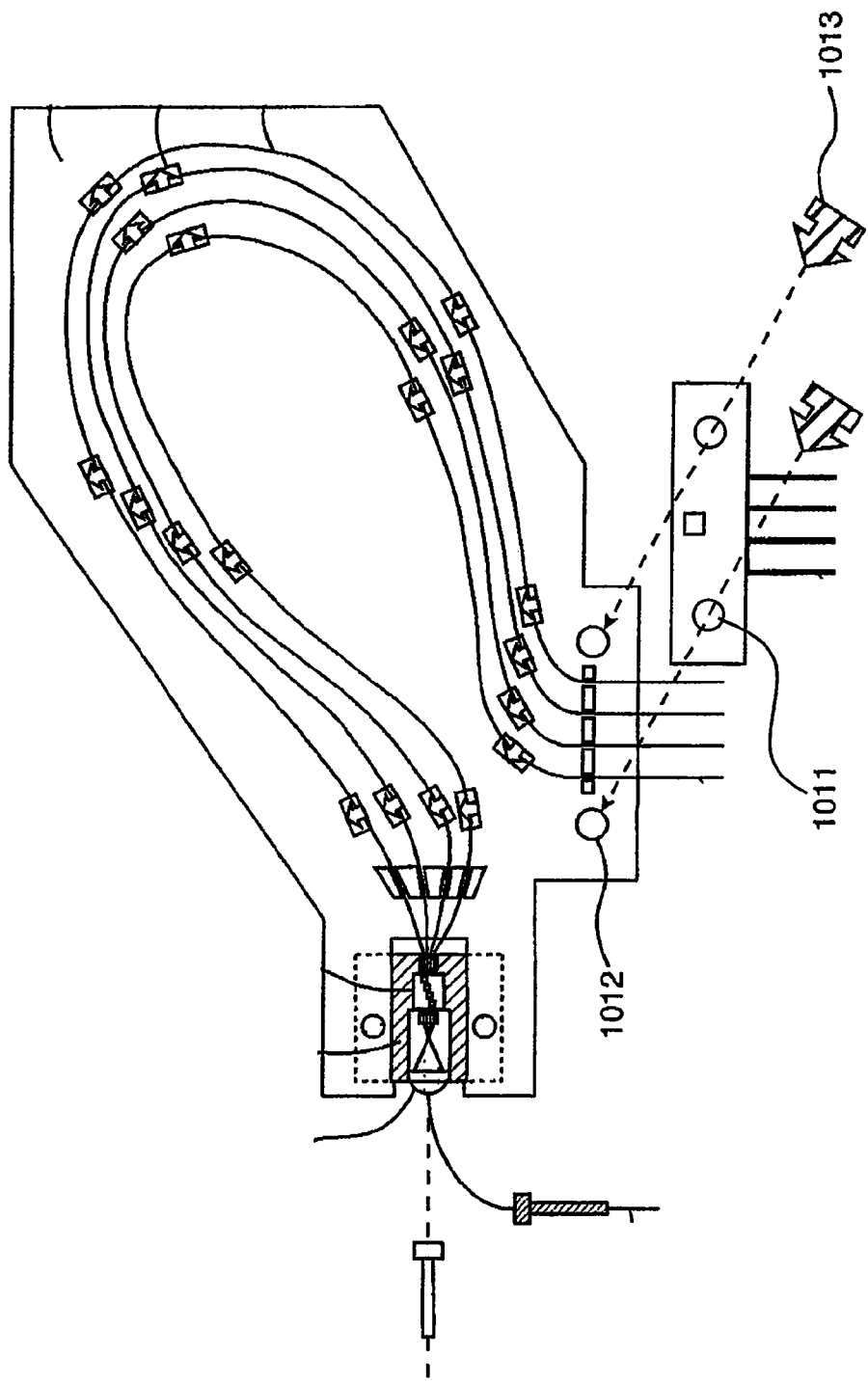
FIG. 10 shows an example of securing an electrode holder and a support plate by fixing pins.

As shown in FIG. 10, holes 1012 for positioning the electrode are formed in the support plate and holes 1011 for positioning are also formed in an electrode holder. The electrode can be attached by aligning them and fixing using fixing pins 1013. Further, the fixing pins can also be made detachable by a user.

According to this embodiment, by fixing the support plate and the electrode holder using the detachable pins, the electrode holder can be handled as an external part. Accordingly, it is not necessary that one electrode holder is disposed to one capillary array but the electrode holder can be recycled again and again by cleaning the same.

Fourth Embodiment

A fourth embodiment of the invention is an example of providing with support clips 1112 a support plate 1102 on the side of the capillary head, and the support plate 1102 also has a function of holding the capillary head 1107. Description is to be made mainly for the difference from the first embodiment.

Figure 11:
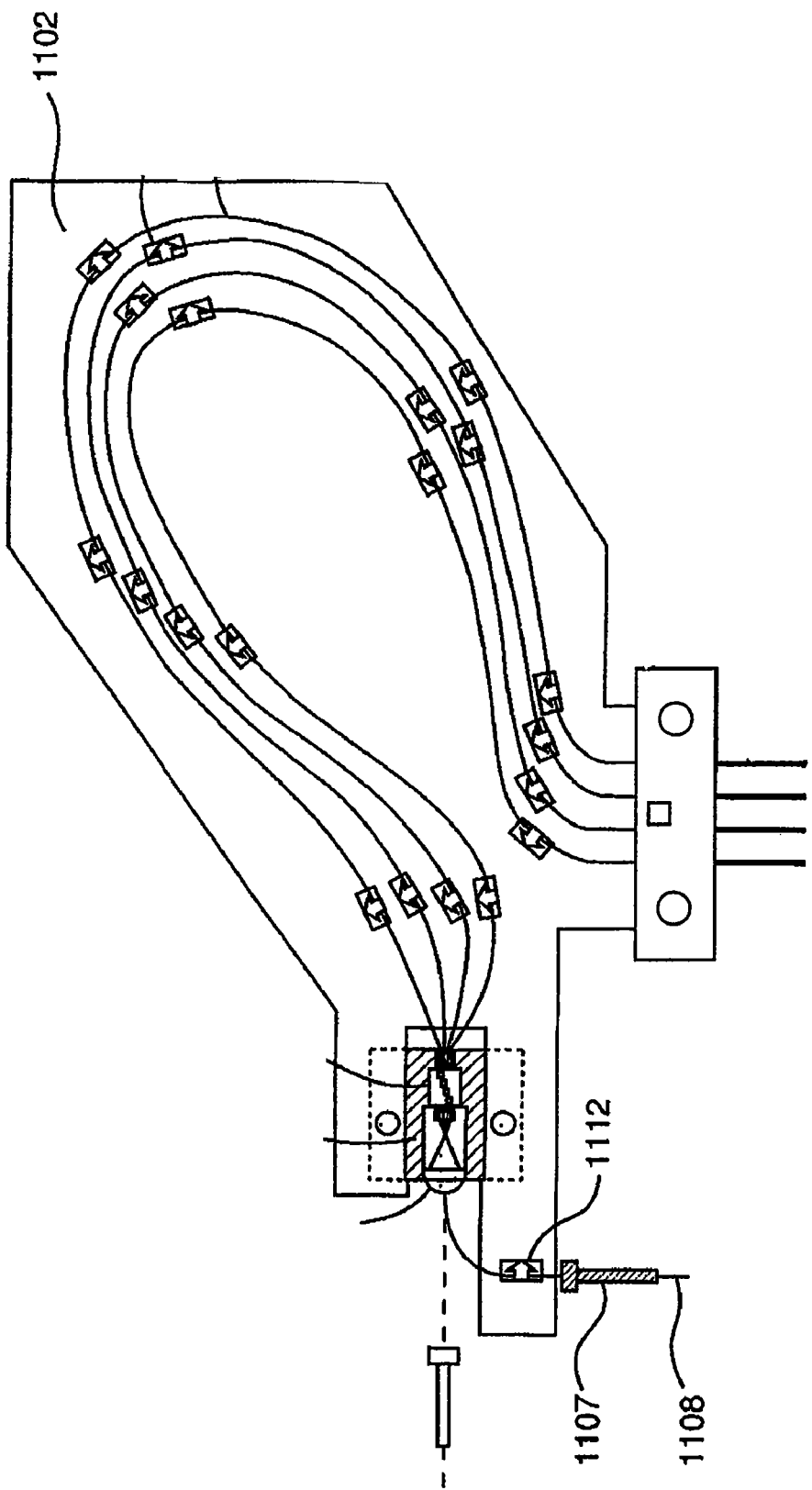
FIG. 11 shows an example of a support plate for supporting a capillary head.

FIG. 11 shows an outline of a support plate for supporting a capillary head. In this embodiment, a capillary between a detection region and a phoretic medium injection end is supported by a support plate. This enables a user to handle a capillary array easily without dangling a capillary head 1107 upon handling the capillary array. Further, by making the capillary head 1107 movable without completely fixing the same, mounting of the capillary head 1107 on the electrophoresis apparatus is facilitated. Further, the capillary head 1107 can be simply mounted on the apparatus by holding the capillary head 1107 such that the position is aligned with the polymer injection port on the side of the apparatus.

Fifth Embodiment

A fifth embodiment of the invention is an example of changing the method of irradiating an excitation light and introducing the excitation light by way of an optical fiber. Description is to be made mainly for the difference from the first embodiment.

Figure 12:
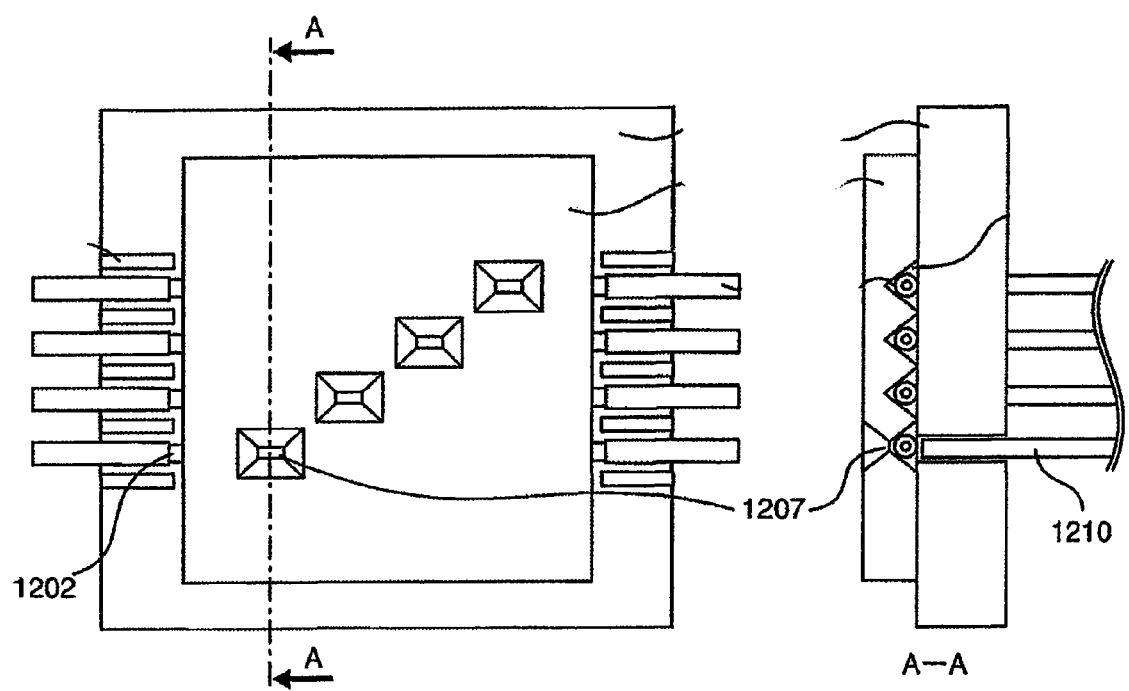
FIG. 12 is an example of introducing an excitation light by an optical fiber.

FIG. 12 shows an outline of a detection section of this embodiment. An excitation light is not introduced in the longitudinal direction of capillary by a condensing lens but an excitation light is introduced from the back of a window hole 1207 using an optical fiber 1210 and irradiated to the capillary.

In this embodiment, a condensing lens is not necessary and a polyimide coating film for the capillary may be removed only at a portion where the excitation light enters. Since the length of a quartz tube exposed portion 1202 of the capillary is short, this can prevent disadvantage such as breaking of the capillary to improve the yield of the capillary array.

Sixth Embodiment

A sixth embodiment of the invention is an example of changing the method of irradiating an excitation light and irradiating a laser light so as to penetrate plural capillaries. Description is to be made mainly for the difference from the first embodiment.

In this embodiment, the vicinity of the excitation light irradiation portion of each capillary is arranged on a detection base plate. The capillaries are arranged substantially parallel to each other and substantially parallel to the detection base plate, and the excitation light irradiation positions for the respective capillaries are arranged substantially on one straight line. The state where capillaries are substantially in parallel with each other and in parallel with the plate means that they are arranged in such parallelism as about within a range of error in view of accuracy.

A laser light oscillated from an argon ion laser light source, etc. is divided by a beam splitter and a mirror into plural components, each of which is restricted for the laser width by a condensing lens and irradiates the capillary from both lateral surfaces of the capillary array. Each of the laser lights is controlled so as to be substantially in parallel with the detection base plate and each of the capillaries and irradiated to the capillary arrangement. Irradiation of the laser light substantially in parallel with each of the capillaries means that the irradiating direction of the laser light is substantially in parallel with a substantial plane constituted by the arrangement of each of the capillaries. The laser light may also be irradiated only on one side. In a case where the laser light is irradiated in a state where the inside of each of the capillaries is filled with a phoretic medium, since the laser light propagates in the capillary arrangement, all the capillaries can be simultaneously irradiated efficiency.

Seventh Embodiment

A seventh embodiment of the invention is an example of changing the method of irradiating an excitation light and irradiating a spread beam so as to irradiate a plurality of capillaries. Description will be made main for the difference from the first embodiment and the sixth embodiment.

In this embodiment, a laser oscillated from a laser light source is expanded by a beam expander, converged into a linear shape by a cylindrical lens, and simultaneously irradiated to all the capillaries in perpendicular to the surface of arrangement of the capillaries. This enables to irradiate a laser light at substantially the same laser intensity to all of the capillaries.

Eighth Embodiment

An eighth embodiment of the invention is an example of changing the method of irradiating excitation light and irradiating a laser beam so as to scan a plurality of capillaries. Description will be made mainly to the difference from the first embodiment, the sixth embodiment and the seventh embodiment.

In this embodiment, a laser light oscillated from a laser light source is reflected on a mirror, condensed by an objective lens, and irradiated to a laser irradiation position of a capillary. The mirror and the objective lens constitute a driving unit and conduct high speed reciprocal driving in the same direction along the direction of the arrangement of each of the capillaries. Thus, each of the capillaries is irradiated under scanning successively by the laser light.

Ninth Embodiment

In a ninth embodiment of the invention, a protruding region or a turn-back region is provided at the peripheral edge of the support plate. The protruding or turn-back region may be continuous or may be a plurality of small regions. Further, a step is formed on the heater or the oven lid so as not to crush the region on the side of the oven. This can provide an advantage of increasing the strength of the support plate and making it less bending.

Tenth Embodiment

In a tenth embodiment of the invention, a grip is provided to a portion of a support base. This can provide an advantage of further facilitating carrying of the capillary array and a setting thereof to the apparatus by a user. Simply grip may be a hole apertured such that a finger can be inserted in a portion of the support plate.

Note that the shapes and structures of the respective elements shown in the above-described embodiments are merely given as an example of implementation of the present invention, and the technical scope of the present invention is not limitedly interpreted with these shapes and structures. That is, the present invention can be implemented in various forms without departing from its sprit and its principal features.

As many apparently widely different embodiments of the present invention can be made without departing from the spirit and scope thereof, it is to be understood that the invention is not limited to the specific embodiments thereof except as defined in the appended claims.

What is claimed is:

1. An electrophoresis apparatus including:
   a plurality of capillaries that can be filled with a phoretic medium;
   a support plate having the plurality of capillaries arranged on the surface thereof;
   a heater in direct contact with the plurality of capillaries and the surface of a support plate to directly control the temperature of the plurality of capillaries;
   a power supply that applies a voltage on both ends of a capillary; and
   an optical system that irradiates an excitation light to an electrophoretically separated sample and detecting fluorescence from the sample.

2. An electrophoresis apparatus according to claim 1, wherein
   the support plate supports a detection base plate in which the plurality of capillaries irradiated with the excitation light are arranged and disposed.

3. An electrophoresis apparatus according to claim 1, wherein
   the support plate has an electrode holding member holding a plurality of electrodes corresponding to the plurality of capillaries.

4. An electrophoresis apparatus according to claim 1, further including a phoretic medium filling mechanism that fills a phoretic medium from a phoretic medium injection end of the plurality of capillaries, wherein the support base supports a capillary head that bundles the phoretic medium injection ends of the plurality of capillaries and can be connected with the phoretic medium filling mechanism.

5. An electrophoresis apparatus according to claim 4, wherein
   a plurality of phoretic medium injection ends are held being protruded from the capillary heads, and
   the plural phoretic medium injection ends are directed downward when the capillary head is connected with the phoretic medium filling mechanism.

6. An electrophoresis apparatus according to claim 4, wherein
   the support plate movably supports the capillary heads.

7. An electrophoresis apparatus according to claim 1, wherein
   the support base has a light shielding member covering the plurality of capillaries arranged in parallel and has plural detection windows for transmitting fluorescence from samples, and
   plural detection windows are not arranged in the direction substantially perpendicular to the capillaries.

8. An electrophoresis apparatus according to claim 7, wherein
   the detection windows are arranged stepwise.

9. An electrophoresis apparatus according to claim 1, wherein
   a light permeable region capable of transmitting a light is provided on the portion of the support base,
   a portion of the plurality of capillaries is disposed on a light transmission region, and
   an excitation light is irradiated to the capillaries on the side opposite to the surface of the support plate on which the capillaries are fixed.

10. An electrophoresis apparatus according to claim 1, wherein
    a portion of the capillary is fixed to the support base plate and the plurality of capillaries are arranged as a capillary array.

11. An electrophoresis apparatus according to claim 1, wherein
    the plurality of capillaries arranged on the support plate do not intersect with each other.

* * * * *